US006221360B1

United States Patent
Chowdhury

(10) Patent No.: US 6,221,360 B1
(45) Date of Patent: *Apr. 24, 2001

(54) INFECTIOUS BOVINE RHINOTRACHEITIS VACCINES AND METHODS

(75) Inventor: Shafiqul I. Chowdhury, Manhattan, KS (US)

(73) Assignee: Kansas State University Research Foundation, Manhattan, KS (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/607,323

(22) Filed: Feb. 26, 1996

(51) Int. Cl.$^7$ .......................... A61K 39/265; C12N 7/01; C12N 7/04

(52) U.S. Cl. ...................................... 424/199.1; 435/235.1; 435/320.1; 435/236; 424/229.1

(58) Field of Search ............................ 424/199.1, 184.1, 424/94.1, 229.1; 435/240.2, 5, 69.1, 69.3, 172.3, 183, 235.1, 252.3, 320.1, 236; 580/395, 350; 536/23.1, 23.72; 935/65

(56) References Cited

U.S. PATENT DOCUMENTS

| | | |
|---|---|---|
| 4,703,011 | 10/1987 | Kit et al. . |
| 4,824,667 | 4/1989 | Kit et al. . |
| 5,128,129 | 7/1992 | Kit et al. . |
| 5,151,267 | 9/1992 | Babiuk et al. . |
| 5,593,873 * | 1/1997 | Cochran et al. ................... 435/320.1 |

FOREIGN PATENT DOCUMENTS

| | | |
|---|---|---|
| 0326127 | 8/1989 | (EP) . |
| WO 92 21751 * | 12/1992 | (WO) ............................ C12N/15/00 |
| 9424296 | 10/1994 | (WO) . |

OTHER PUBLICATIONS

Babiuk et al. Protection of Cattle from Bovine Herpesvirus Type I (BH–1) Infection by Immunization with Individual Viral Glycoproteins. Virology. vol. 159, pp. 57–66, 1987.*
Peterson et al. Propagation and Quantitation of Animal Herpesviruses in Eight Cell Culture Systems. Comp. Immun. Microbiol. Infect. Dis. vol. 11, No. 2, pp. 93–98, 1988.*
Faecking, M et al. Powerful and versatile enhancer–promoter unit for mammdiam expression vectors Gene, 45(1986) 101–105.*
Kit S, et al. Expression of porcine pseudorabies virus genes by a bovine herpes virus–1(infections bovine rhinotracheitis virus) fector. Arch virol. (1992) 124=1–20.*
Bello, L. et al, Virology 190:666–673, 1992.*
Stinski, in Fundamental Virology, Second edition, ed. B.N. Fields et al, Raven Press, p. 929–950), 1991.*
Miller et al, Am. J. Vet. Res. 56(7):870–874, Jul. 1995.*

Tikoo et al. Advances in Virus Research 45:191–223, 1995.*
Abdelmagid et al.; Fine Mapping of Bovine Herpesvirus–1 (BHV–1) Glycoprotein D (gD) Neutralizing Epitopes by Type–Specific Monocolonal Antibodies and Sequence Comparison With BHV–5 gD; Virology 206, 242–253 (1995).
Bello et al.; Sequence and Transcript Analysis of the Bovine Herpesvirus 1 Thymidine Kinase Locus; Virology 189, 407–414 (1992).
Chowdhury; Molecular Basis of Antigenic Variation between the Glycoproteins C of Respiratory Bovine Herpesvirus 1 (BHV–1) and Neurovirulent BHV–5; Virology 213, 558–568 (1995).
Chowdhury et al.; Transinhibition of herpes simplex virus replication by an inducible cell–resident gene encoding a dysfunctional VP19c capsid protein; Virus Research 33, 67–87 (1994).
Chowdhury et al.; Molecular biological characterization of engine herpesvirus type 1 (EHV–1) isolates from ruminant hosts; Virus Research 11, 127–129 (1988).
Chowdhury et al.; Equine Herpesvirus Type 1 (EHV–1) Induced Abortions and Paralysis in a Lippizzaner Stud: a Contribution to the Classification of Equine herpesvirus; Arch. Virol 90, 273–288 (1986).
Field et al.; The pathogenicity of thymidine kinase–deficent mutants of herpes simplex virus in mice; J. Hyg., Camb. 81, 267 (1978).
Fitzpatrick et al.; Nucleotide Sequence of Bovine Herpesvirus Type 1 Glycoprotein gIII, a Structural Model for gIII as a New Member of the Immunoglobulin Superfamily, and Implications for the Homologous Glycoproteins of Other Herpesviruses; Virolgy 173, 46–57(1989).
Holland et al.; Physical Mapping of the Mutation in an Antigenic Variant of Herpes Simplex Virus Type 1 by Use of an Immunoreactive Plaque Assay; Journal of Virology, May 1983, p. 649–652, vol. 46, No.2.
Kit et al.; Thymidine Kinase–negative Bovine Herpesvirus Type 1 Mutant Is Stable and Highly Attenuated in Calves; Archives of Virology, 86, 63–83 (1985).

(List continued on next page.)

Primary Examiner—Mary E. Mosher
(74) Attorney, Agent, or Firm—Hovey, Williams, Timmons & Collins

(57) ABSTRACT

The disclosed invention is directed to (1) recombinant bovine herpesvirus genes having foreign genes inserted therein, (2) infectious recombinant bovine herpesviruses carrying these recombinant genes, (3) methods of producing these recombinant bovine herpesviruses, (4) methods of immunizing animals against diseases caused by bovine herpesviruses using these recombinant bovine herpesviruses as vaccines, and (5) methods of detecting infection of an animal by these recombinant bovine herpesviruses. In its preferred form, the invention is directed to the construction of an infectious recombinant bovine herpesvirus type 1 having a functional β-galactosidase gene inserted in and thereby inactivating the thymidine kinase gene (e.g., Gal-TK); infection of an animal with the resultant avirulent vaccine virus is detected by assaying the animal's respiratory secretions for the presence of virus having β-galactosidase activity in host cells.

18 Claims, 8 Drawing Sheets

OTHER PUBLICATIONS

Kousoulas, et al., Mutations Affecting Comformation of Sequences of Neutralizing Epitopes Identified by Reactivity of Viable Plaques Segregate from *syn* and *ts* Domains of HSV–1(f) gB Gene; Virology, 135, 379–394 (1984).

Leung–Tack et al.; The Complete DNA Sequence and the Genetic Organization of the Short Unique Region ($U_s$) of the Bovine Herpesvirus Type 1 (ST Strain); Virology 199, 409–421 (1994).

Mayfield et al.; Cloning and Cleavage Site Mapping of DNA from Bovine Herpesvirus 1 (Cooper Strain); Journal of Virology, Jul. 1980, p. 259–264.

Misra et al.; Proteins Specified by Bovine Herpesvirus 1 (Infectious Bovine Rhinotracheitis Virus); Journal of Virology, Nov. 1981, p. 367–378.

Mittal et al,; Analysis of the Bovine Herpesvirus Type 1 Thymidine Kinase (TK) Gene from Wild–type Virus and TK–deficiency Mutants; J. Gen. Virology (1989), 70, 901–918.

Rigby et al,; Labeling Deoxyribonucleic Acid to High Specific Activity in Vitro by Nick Translation with DNa Polymerase I; J. Mol. Biol. (1977) 113, 237–251.

Smith et al.; The location and nucleotide sequence of the thymidine kinase gene of bovine herpesvirus type 1.2; Journal of Gen. Virology (1990), 71, 2417–2424.

Weinmaster et al.; Bovid Herpesvirus Type–1 (Infectious Bovine Rhinotracheitis Virus)–Induced Thymidine Kinase, Virology 118, 191–201 (1982).

Whitbeck et al.; Chararacterization of the Bovine Herpesvirus 1 Homolog of the Herpes Simplex Virus 1 UL24 Open Reading Frame; Virology 200, 263–270 (1994).

Wyler et al.; Infectious Bovine Rhinotracheitis/Vulvovginitis (BHV1); Institute of Virology (No date).

Liang et al.; Ab in Vitro Study of a glycoprotein gIII–negative bovine herpesvirus 1 (BHV–1) mutant expressing β–galactosidase: Evaluation of the role of gIII in virus infectivity and its use as a vector for mucosal immunization; virol. 189, 629–639 (1992).

Kaashoek, et al.; Virulence and immunogenicity in calves of thymidine kinasse– and glycoprotein E–negative bovine herpesvirus 1 mutants; Vet. Micro. 48, 143–153 (1996).

van Engelburg et al.; A gylcoprotein E deletion mutant of bovine herpesvirus 1 is avirulent in calves; J. Gen. Virology, 75, 2311–2318 (1994).

* cited by examiner

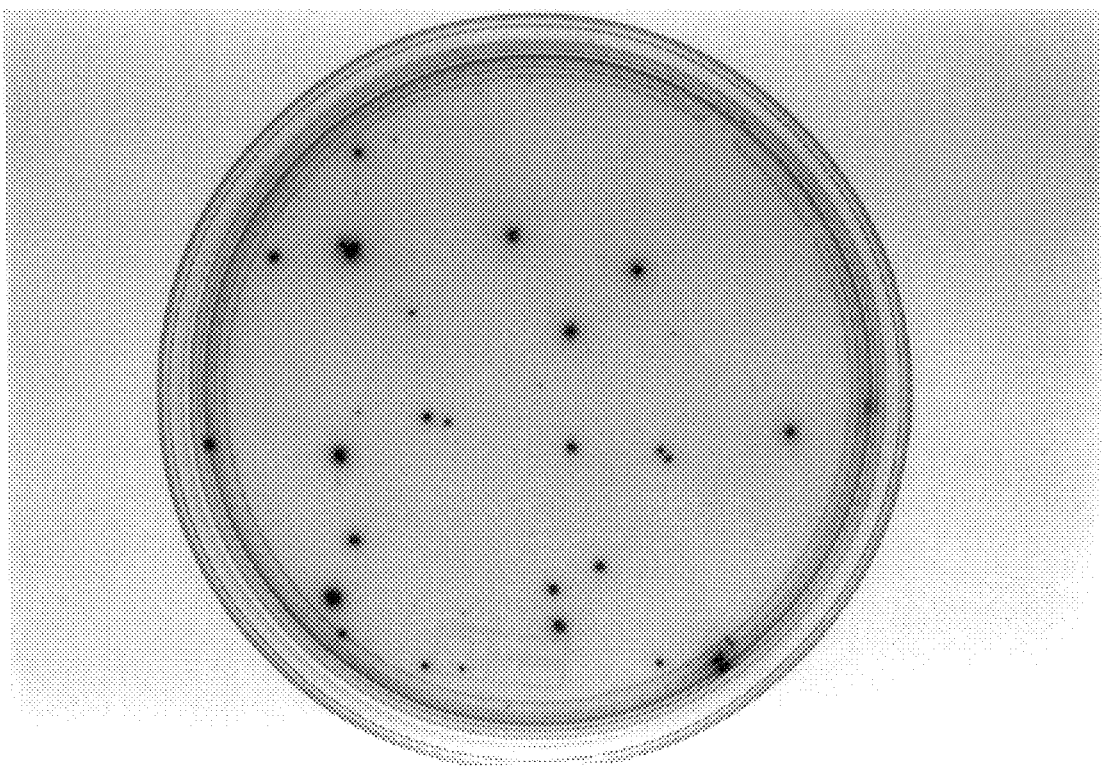
Fig.3A.
Fig.3B.
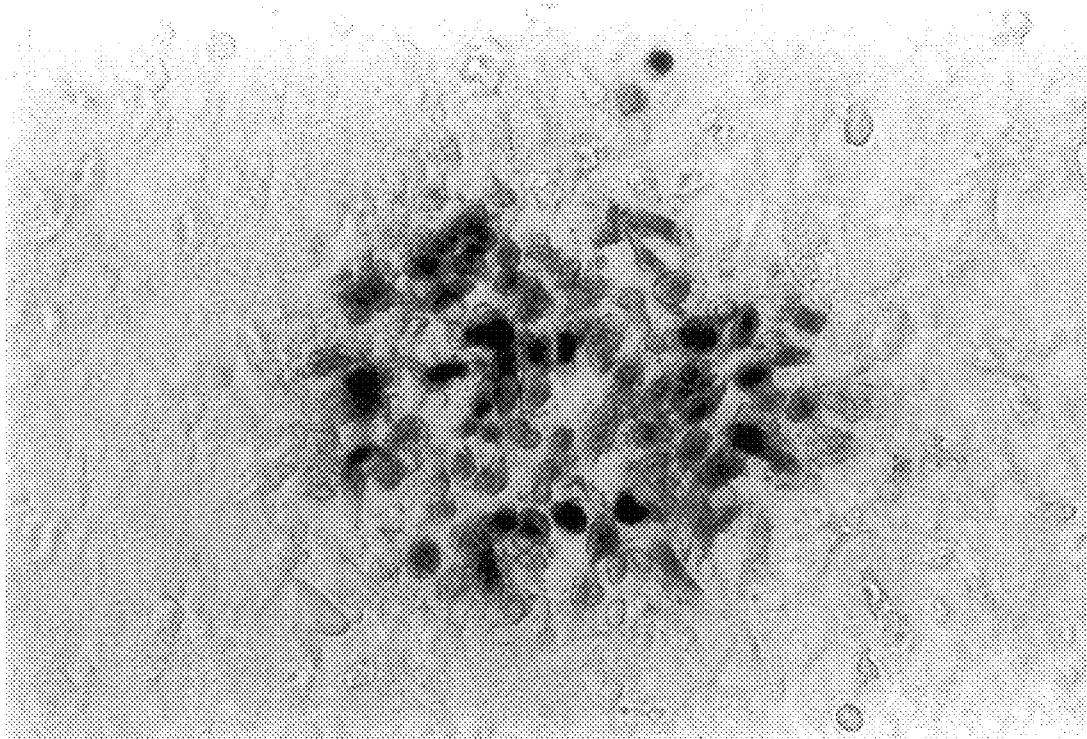

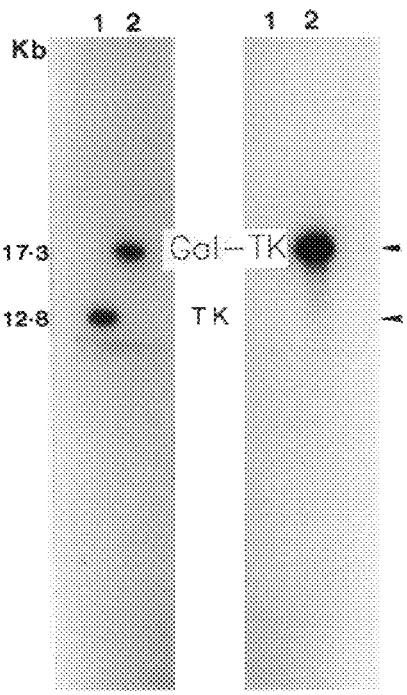 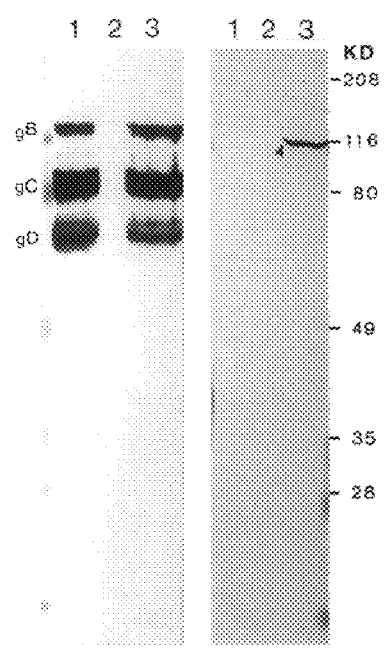
Fig.4A. Fig.4B. Fig.5A. Fig.5B.

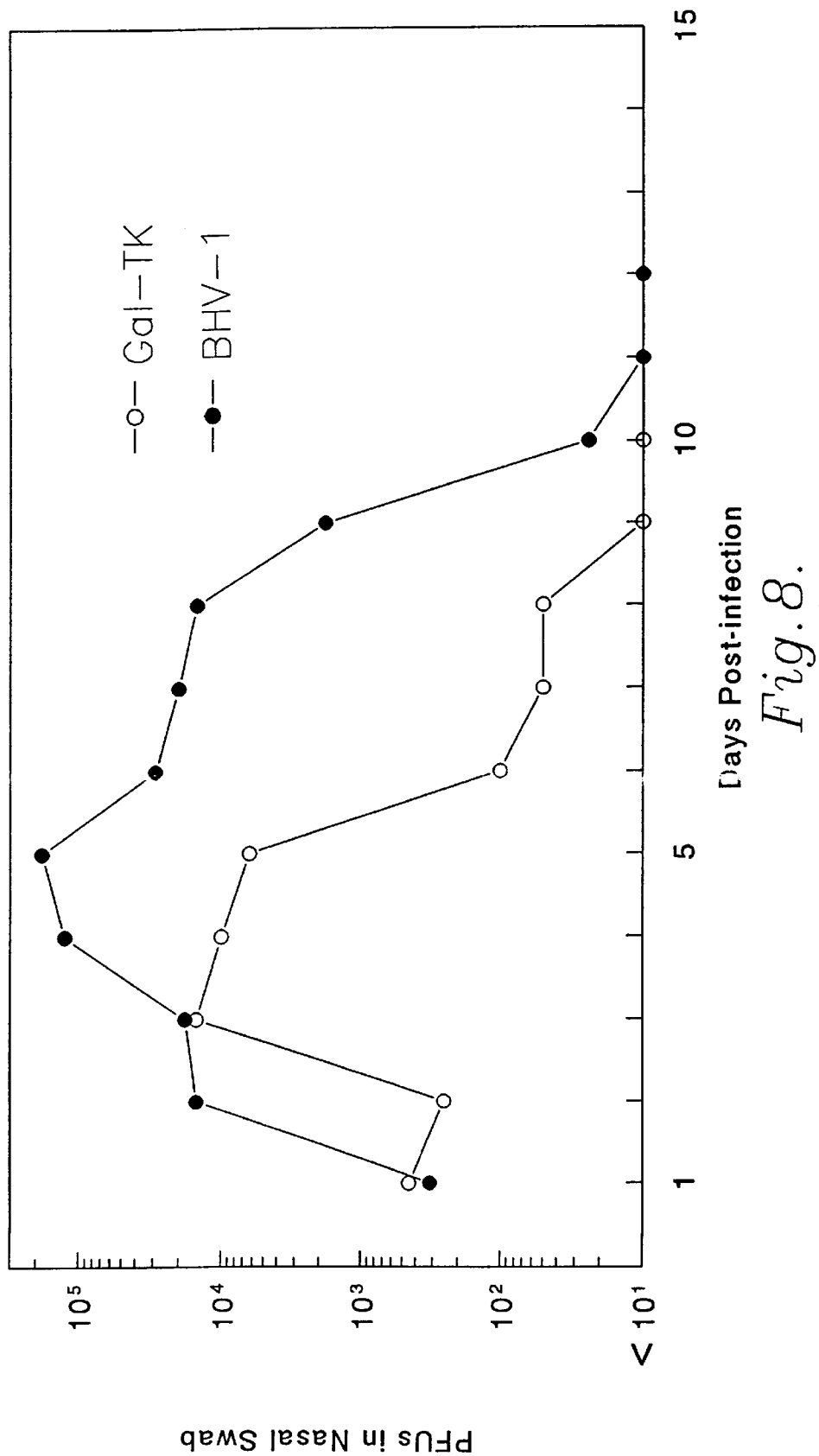

INFECTIOUS BOVINE RHINOTRACHEITIS VACCINES AND METHODS

BACKGROUND OF THE INVENTION

1. Field of the Invention

The present invention is broadly concerned with vaccines composed of recombinant bovine herpesviruses and corresponding methods. More particularly, in its preferred form, the present invention is concerned with the construction of an infectious recombinant bovine herpesvirus type 1 having a functional β-galactosidase gene inserted in and thereby inactivating the thymidine kinase gene (e.g., Gal-TK); infection of an animal with the resultant avirulent vaccine virus is detected by assaying the animal's respiratory secretions for the presence of virus having β-galactosidase activity in host cells.

2. Description of the Prior Art

Bovine herpesvirus type 1 (BHV-1), also known as infectious rhinotracheitis virus (IBR), is associated with a variety of clinical diseases including rhinotracheitis, conjunctivitis, genital infections, abortion, enteritis, encephalitis, and generalized systemic infections in cattle (Ludwig, 1983; Wyler et al., 1989). The genome of BHV-1 consists of a linear double-stranded DNA molecule about 140-kb in length and is composed of a unique long ($U_L$) region and a unique short ($U_S$) region. The $U_s$ region is flanked by an internal and a terminal inverted repeat sequence ($I_R$ and $T_R$, respectively). The BHV-1 genome encodes approximately 70 proteins (Misra et al., 1981). Many herpesviruses, including BHV-1, encode thymidine kinase (TK) (Kit and Qavi, 1983; Weinmaster et al., 1982). The BHV-1 TK gene has been mapped (Bello et al., 1987), and the sequences of the TK genes of four BHV-1 strains have been determined. (Kit and Kit, 1987; Mittal and Field, 1989; Smith et al., 1990; Bello et al., 1992).

The TK genes of these four strains encode between 357 and 359 amino acid (aa) residues. The deduced aa sequences of these genes reveal that BHV-1 TK is composed of five protein domains (I–V). These domains have a high degree of homology to corresponding domains in TKs of other herpesviruses, suggesting that these domains have functional significance.

The TK gene is not essential for replication of BHV-1 in vitro or in vivo (Kit and Kit, 1987; Mittal and Field, 1989), but does play an important role in pathogenicity. BHV-1 and other herpesviruses having defective TK genes grow normally in vitro but are highly attenuated in vivo (Field and Wildy, 1978; Kit et al., 1985 a, b; Slater et al., 1993). Thus, the basis of several BHV-1 vaccines has been inactivation of the TK gene (Kit and Qavi, 1983; Kit and Kit, 1987; Kit and Kit, 1989).

SUMMARY OF THE INVENTION

The present invention is directed to (1) recombinant bovine herpesvirus genes having foreign genes inserted therein, (2) infectious recombinant bovine herpesviruses carrying these recombinant genes, (3) methods of producing these recombinant bovine herpesviruses, (4) methods of immunizing animals against diseases caused by bovine herpesviruses using these recombinant bovine herpesviruses as vaccines, and (5) methods of detecting infection of an animal by these recombinant bovine herpesviruses. The invention is unique and unknown in the prior art in that a foreign gene within a bovine herpesvirus gene carried by an infectious recombinant bovine herpesvirus may serve dual purposes. First, the foreign gene may inactivate a bovine herpesvirus gene required for virulence, thereby resulting in an attenuated virus suitable for a vaccine. Second, if the foreign gene is expressed, detection of the product of the foreign gene in an animal demonstrates that the animal has been infected with the recombinant bovine herpesvirus.

In the first preferred embodiment, the recombinant bovine herpesvirus gene has a foreign gene inserted therein. Advantageously, the recombinant bovine herpesvirus gene is a bovine herpesvirus type 1 gene encoding thymidine kinase, and the foreign gene is a hybrid gene having a promoter and a coding region from different organisms. Preferably, the promoter is the immediate early promoter from human cytomegalovirus, and the coding region encodes a β-galactosidase (e.g., *Escherichia coli* β-galactosidase). This recombinant bovine herpesvirus gene is ideally the recombinant bovine herpesvirus gene carried by pGal-TK.

In the second preferred embodiment, the infectious recombinant bovine herpesvirus carries a recombinant bovine herpesvirus gene described in the first preferred embodiment. Advantageously, this recombinant bovine herpesvirus gene is at least partially inactive and produces no functional product in a host cell, and in its most preferred form encodes thymidine kinase and produces no functional thymidine kinase in a host cell. Preferably, the foreign gene inserted within the recombinant bovine herpesvirus gene is expressed and produces *Escherichia coli* β-galactosidase in a host cell. The recombinant bovine herpesvirus is ideally attenuated or avirulent (e.g., Gal-TK). Additionally, the recombinant bovine herpesvirus may have at least part of one or more glycoprotein gene(s) not essential for viral replication (e.g., the glycoprotein E gene, the glycoprotein I gene, and the glycoprotein C gene) deleted.

In the third preferred embodiment, an infectious recombinant bovine herpesvirus described in the second preferred embodiment is produced as follows: A hybrid DNA molecule composed of a cloning vector and a recombinant bovine herpesvirus gene described in the first preferred embodiment is constructed. Advantageously, the cloning vector and the hybrid DNA molecule is a plasmid (e.g., pGal-TK). Host cells (e.g., Madin-Darby bovine kidney cells) are co-transfected with this hybrid DNA molecule and with infectious DNA from a bovine herpesvirus (e.g., bovine herpesvirus type 1). The resultant recombinant bovine herpesvirus is subsequently recovered. Preferably, after co-transfection and before recovery, the recombinant bovine herpesvirus is enriched. Ideally, this enrichment consists of passage of the recombinant bovine herpesvirus through host cells in the presence of at least one chemical (e.g., thymidine arabinoside and/or 5-bromo-2'-deoxyuridine) that selects for the growth of thymidine kinase-inactivated virus. Preferably, after enrichment and before recovery, bovine herpesviruses are screened by detecting the foreign gene product. Ideally, this product is an *Escherichia coli* β-galactosidase which is detected by the hydrolysis of a β-galactosidase substrate (e.g., halogenated indolyl-β-D-galactoside). Additionally, one or more glycoprotein gene(s) not essential for viral replication (e.g., the glycoprotein E gene, the glycoprotein I gene, and the glycoprotein C gene) may be deleted from the recombinant bovine herpesvirus.

In the fourth preferred embodiment, an animal is immunized against disease caused by bovine herpesvirus by making a vaccine composed of an infectious recombinant bovine herpesvirus described in the second preferred embodiment in a pharmaceutically acceptable carrier (e.g., a cell culture medium), and administering this vaccine to the animal, ideally by spraying the vaccine into the animal's nostrils. Additionally, the recombinant bovine herpesvirus vaccine strain may have at least part of one or more glycoprotein gene(s) not essential for viral replication (e.g., the glycoprotein E gene, the glycoprotein I gene, and the glycoprotein C gene) deleted.

In the fifth preferred embodiment, an animal vaccinated as described in the fourth embodiment is tested to determine whether the animal has been infected by an infectious recombinant bovine herpesvirus described in the second preferred embodiment. Advantageously, a specimen is obtained from the vaccinated animal and is assayed for the presence of a macromolecular unit (e.g., the recombinant bovine herpesviruses themselves) produced by the vaccinated animal in response to infection. Ideally, the specimen is a respiratory secretion, and the assay comprises assaying the respiratory secretion for the presence of recombinant bovine herpesviruses that produce β-galactosidase in host cells by detecting the hydrolysis of a β-galactosidase substrate (e.g., halogenated indolyl-β-D-galactoside).

Plasmid Gal-TK and Gal-TK have been deposited in the American Type Culture Collection, Rockville, Md. under the terms of the Budapest Treaty and have been accorded Accession Nos. 97326 and VR-2519, respectively.

BRIEF DESCRIPTION OF THE DRAWINGS

FIGS. 3(A–B) are photographs showing gross (FIG. 3A) and microscopic (FIG. 3B) views of plaques produced by Gal-TK and identified by Bluo-Gal staining;

FIGS. 4(A–B) are photographs of autoradiograms showing Southern-blot analyses of Gal-TK DNA;.

FIGS. 5(A–B) are photographs showing immunoblot analyses of major glycoproteins (FIG. 5A) and β-gal (FIG. 5B) synthesized by Gal-TK;

FIG. 8 is a graph showing virus titers in nasal secretions from calves after intranasal infection, with each data point representing the average titer of samples obtained from two separate calves.

DETAILED DESCRIPTION OF THE PREFERRED EMBODIMENT

The following example describes the construction of an infectious recombinant BHV-1 having a functional β-gal gene inserted in and thereby inactivating the TK gene, a method of immunizing animals against diseases caused by BHV using this recombinant BHV-1 as a vaccine, and a method of detecting infection of an animal by this virus by assaying the animal's respiratory secretions for the presence of virus having β-gal activity. This example is set forth by way of illustration only, and nothing therein shall be taken as a limitation upon the overall scope of the invention.

Materials and Methods
Virus Strains and Cell Lines

Figure 1:
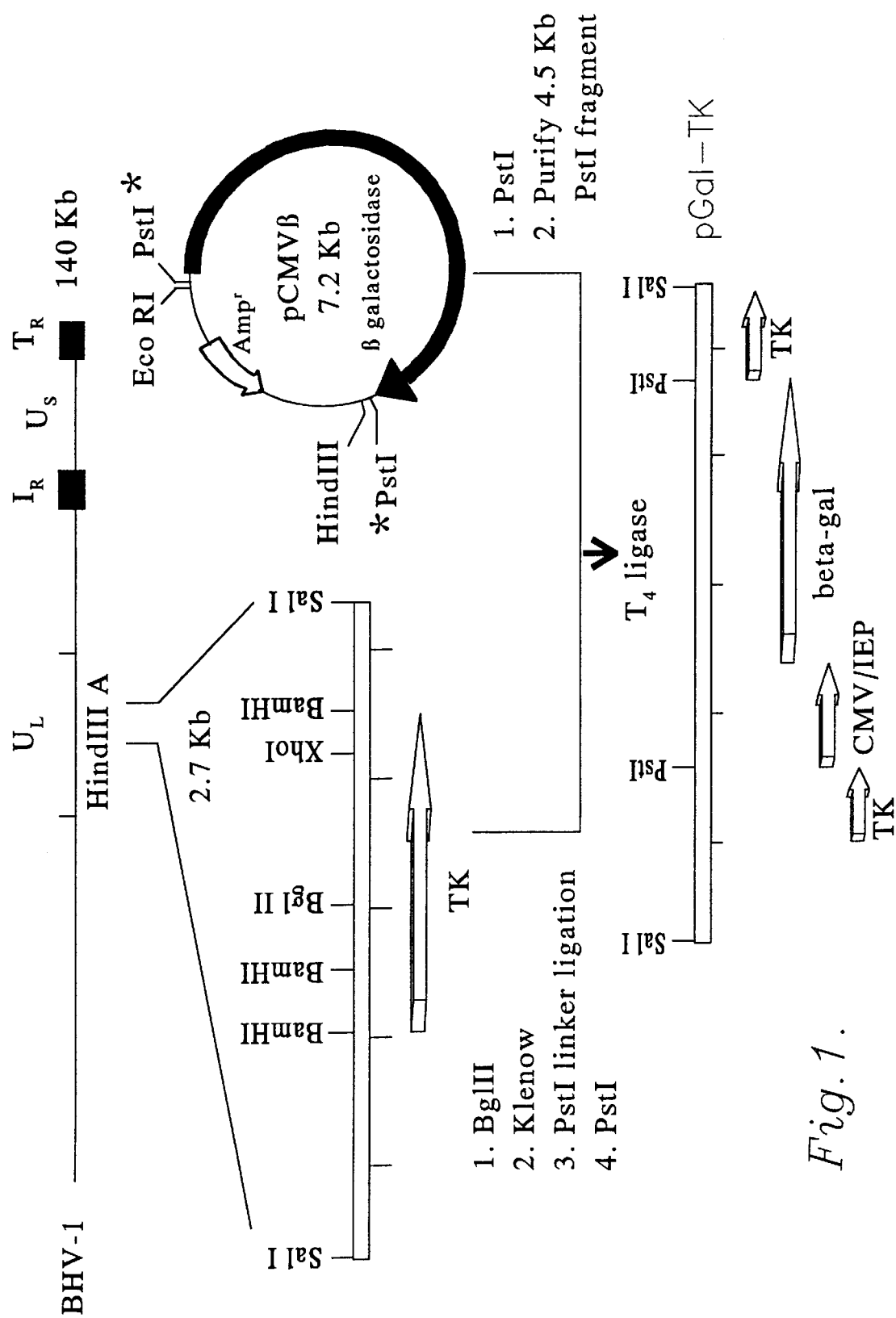
FIG. 1 is a flow diagram outlining the construction of pGal-TK virus, an insertion-vector plasmid containing a functional β-galactosidase (β-gal) gene flanked by TK coding sequences.
Figure 2:
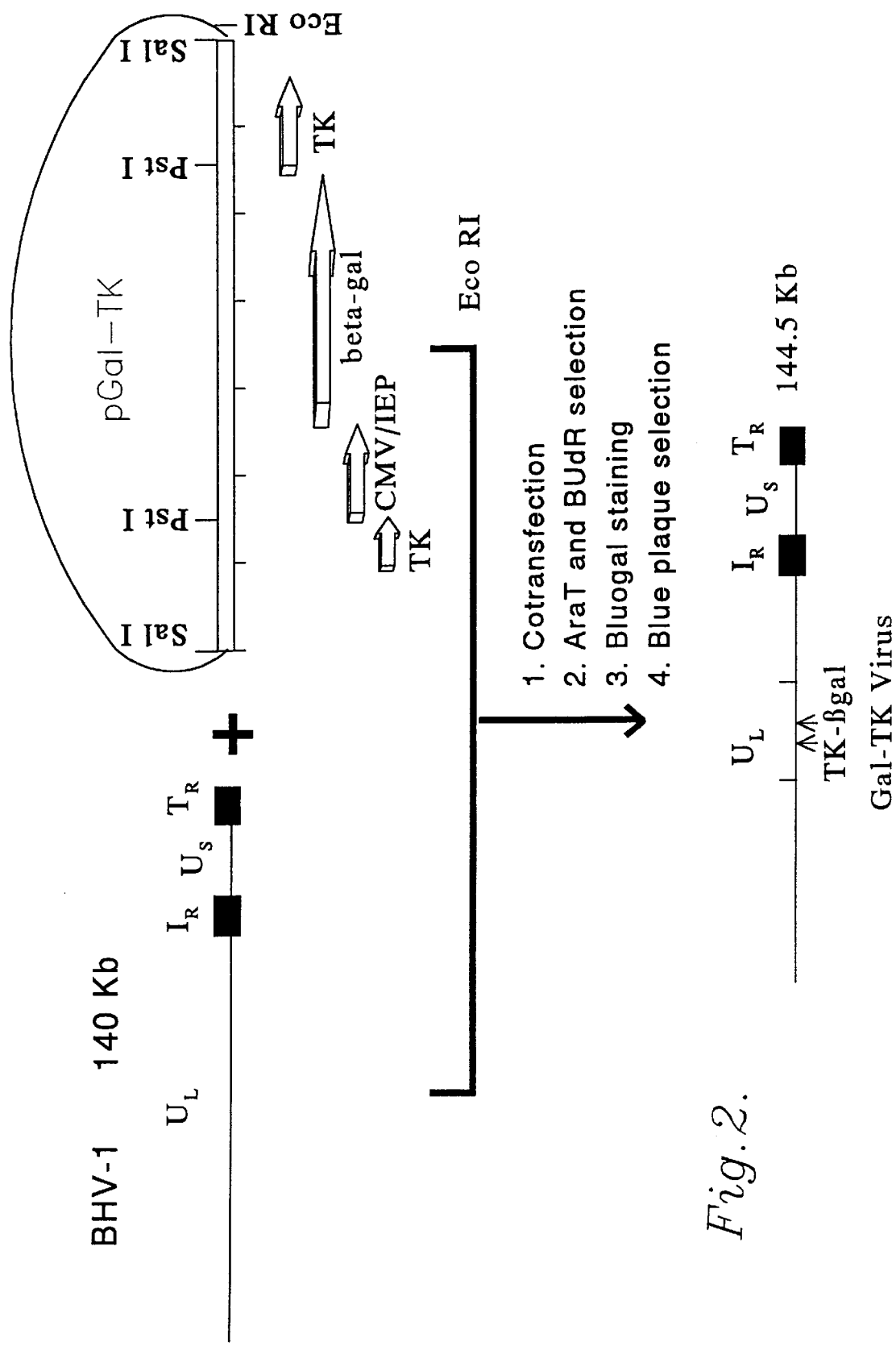
FIG. 2 is a flow diagram outlining the construction of Gal-TK virus, an infectious recombinant bovine herpesvirus type 1 having a functional β-gal gene inserted in and thereby inactivating the thymidine kinase gene.
Figure 6:
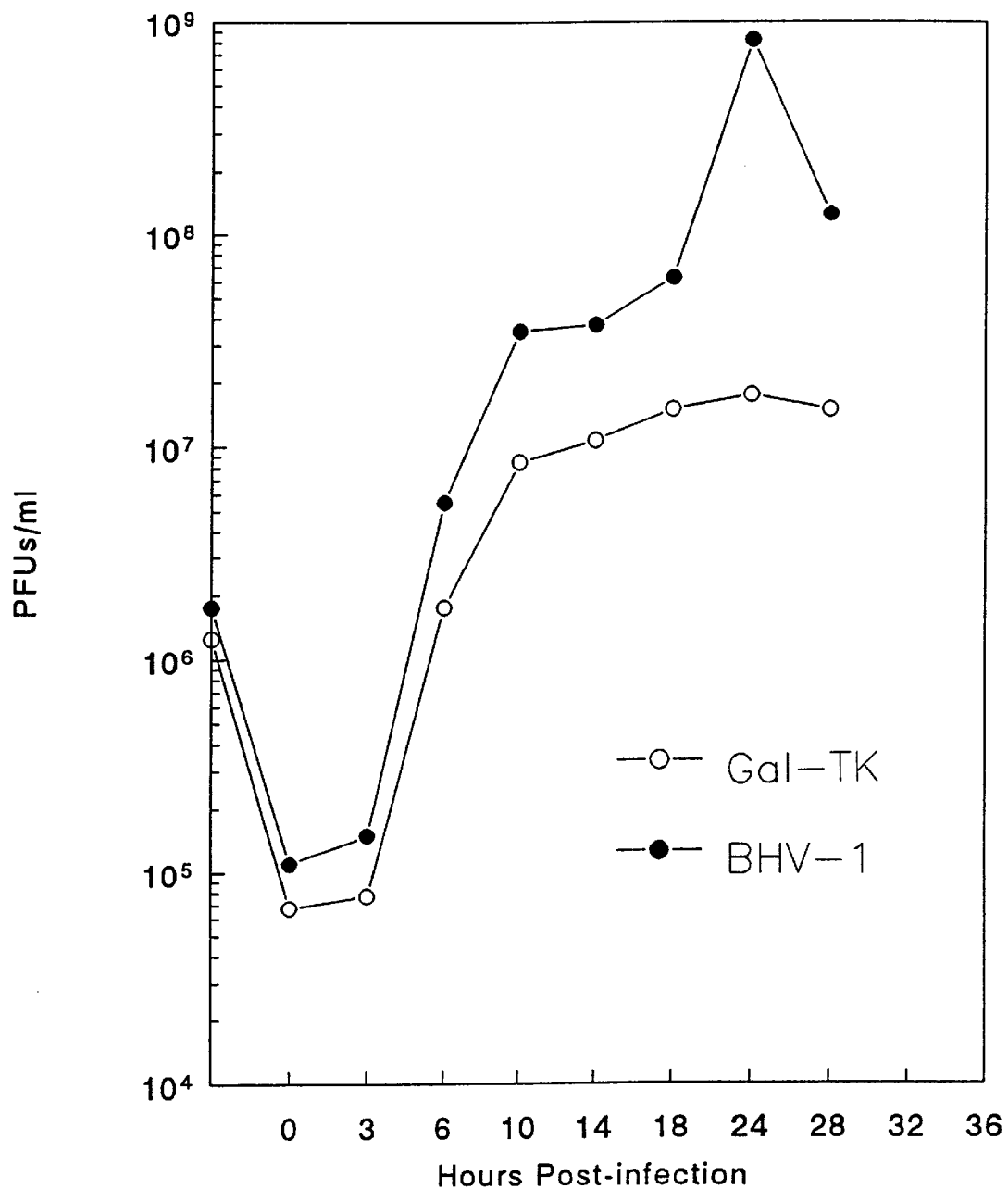
FIG. 6 is a graph showing a one-step growth curve of Gal-TK (○) and BHV-1 (Cooper strain) (●) in MDBK cells, with each data point representing the average of duplicate samples obtained from separate infections.

The Cooper (Colorado-1) strain of BHV-1 was obtained from the American Type Culture Collection (Rockville, Md.). Viruses were propagated and titrated in Madin-Darby bovine kidney (MDBK) cells grown in Dulbecco Modified Eagles Medium (DMEM) supplemented with 10% fetal bovine serum (FBS).
Isolation of Virus DNA DNA was prepared from cell-free supernatant virus using dodecylsulfate and proteinase K lysis, phenol/chloroform extraction, and ethanol precipitation as described previously (Chowdhury et al., 1986).
Sodium Dodecyl Sulfate-Polyacrylamide Gel Electrophoresis (SDS-PAGE) and Western-Blot Analysis SDS-PAGE of proteins from mock- and virus-infected cells was performed under reducing conditions as described previously (Laemli, 1970; Abdelmagid et al., 1995).
Construction of Recombinant Plasmids Containing TK Sequences Plasmid BHA, containing the HindIII-A fragment of BHV-1 DNA, was obtained from Dr. W. Lawrence (U. Pennsylvania, Philadelphia, Pa.). A 2.7-kb SalI fragment containing the TK-coding region of BHV-1 was subcloned from pBHA (FIG. 1). The unique BglII site in the 2.7-kb SalI fragment was changed to a PstI site by PstI-linker ligation. The 4.5-kb PstI fragment of pCMVβ (Clontech, Palo Alto, Calif.) containing the *Escherichia coli* β-gal gene under the control of the human cytomegalovirus (HCMV) immediate early promotor (IEP) was inserted into the above-created PstI site. The resulting plasmid (pGal-TK) contained the sequences coding for the first 156 amino acids (aa) of the TK open reading frame (ORF) (Mittel and Field, 1989) fused to the IEP-regulated β-gal sequences.
Construction of a Recombinant BHV-1 Having a Functional β-gal Gene Inserted in the TK Gene Linearized pGal-TK and BHV-1 (Cooper strain) DNA were used to co-transfect (Chowdhury and Batterson, 1994) MDBK cells (FIG. 2). Briefly, cultures of MDBK cells were plated at a density of $1\times10^6$ cells/25 cm$^2$ flask 5 h before DNA transfection. Linearized pGal-TK was co-precipitated with BHV-1 DNA for 20 min in CaCl$_2$ in a final volume of 0.5 ml and precipitated DNA was added to the cells. After 5–6 h, cells were treated for 2 min with medium containing 15% glycerol and 6% fetal calf serum and then washed twice with medium. After 24 h, each flask containing infected cultures was trypsinized, and cultures were replated into two new 25 cm$^2$ flasks. After incubation at 37° C. for 2 h, the medium was replaced with medium containing 150 μg/ml thymidine arabinoside (AraT) and incubated further at 37° C. for 2–5 days depending upon the CPE (cytopathic effect). The cultures were frozen, thawed, and sonicated, and virus titers were determined. Recombinant viruses at a multiplicity of infection (m.o.i.) of 0.1 were then passaged once in the presence of 150 μg/ml AraT and twice in the presence of 200 μg 5-bromo-2'deoxyuridine (BUdR). MDBK cells in 60-mm petri dishes then were infected with 20–50 plaque-forming units (PFUs) of probable recombinant viruses/plate. After 1 h incubation at room temperature, the cells were overlayed with prewarmed medium containing 600 μg/mi halogenated indolyl-β-D-galactoside (Bluo-Gal; Gibco BRL, Grand Island, N.Y.) in DMEM/2% FBS/0.5% agarose and incubated further at 37° C. for 2–4 days. Recombinant viruses having β-gal activity were selected by the appearance of blue plaques. These viruses were plaque purified three times, and a representative virus (Gal-TK) was selected.

Construction of a Gal-TK Derivative Having a Deletion in the Glycoprotein C (gC) Gene The BHV-1 gC gene has been sequenced previously and is predicted to encode 521 aa (Fitzpatrick et al., 1989). A 3.5-kb BglII/EcoRI fragment containing the BHV-1 gC gene and its flanking sequences is subcloned to give pgC1. A 1071-bp fragment carrying a portion of gC promoter/regulator sequences encoding the first 338 aa of gC is deleted from pgC1 as follows: Plasmid gC1 DNA is digested with BamH1 and XhoI followed by blunt ending the Klenow fragment. The resultant larger fragment is gel purified, ligated, and used to transform Escherichia coli strain DH5 to give p∇gC1. The point of deletion in p∇gC1 is flanked on both sides by BHV-1 specific DNA segments (a 650-bp segment on one side and a 1.7-kb segment on the other side).

MDBK cells are co-transfected with linearized p∇gC1 and Gal-TK DNA. Recombinant viruses having a deleted gC gene are identified by the "white and black plaque method" (Holland et al., 1983; Kousoulos et al., 1984). Briefly, progeny viruses (50–200 PFUs) are plated onto monolayers of MDBK cells. After an adsorption period of 1 h, the cells are overlaid with DMEM containing 5% FBS and 1% of carboxymethyl cellulose. At 3–4 days postinfection, the overlay is removed. After two washes in DMEM, the cells are incubated for 1 h at room temperature with a 1:1000 dilution of monoclonal antibody F2 which is specific for a gC eptiope encoded by the segment deleted in the recombinant progeny (Chowdhury, 1995). After washing the cells four times in DMEM, 1 ml of media containing 5 μl of biotinylated goat anti-mouse IgG is added, followed by incubation for 2 h at room temperature. After washing the cells three times in PBS, 2 ml of avidin-biotin-peroxidase complex (Vectorlabs, Burlingame, Calif.) are added, followed by incubation for 30 min. After washing the cells two or three times in PBS, the cells are incubated in 2 ml substrate solution (10 mg of 4-chloro-1-naphthol dissolved in 1 ml of ethanol, diluted to 100 ml of PBS containing 100 μl of 3% $H_2O_2$). Plaques containing Gal-TK stain black, whereas plaques containing virus having a deleted gC remain unstained (i.e., white). Virus from unstained plaques are plaque purified three times and screened for the gC gene deletion by Western-blot and Southern-blot analyses. A representative gC⁻ Gal-TK derivative is selected as a vaccine strain.

Construction of a Gal-TK Derivative Having a Deletion in the Glycoprotein I (gI) Gene and the Glycoprotein E (gE) Gene A PstI/BamHI fragment (0.63-kb) of pCMVβ containing the HCMV IEP is inserted into the vector pBI101 (Clontech, Palo Alto, Calif.) cleaved with PstI and BamHI. This places the IEP immediately upstream of the β-glucuronidase (GUS) gene. The resulting plasmid (pCMV-GUS) contains an IEP-regulated GUS-gene cassette (2.5-kb) that can be excised by digesting the plasmid with HindIII and EcoRI. Transient expression of GUS is monitored by indirect immunofluorescence using rabbit anti-GUS serum (Clontech, Palo Alto, Calif.).

An EcoRI/EcoRI 16-kb fragment spanning BHV-1 genomic map unit (m.u.) 0.818 to m.u. 0.936 will be cloned into the EcoRI site of pBR 3222. The resulting plasmid pKS400 is digested with XhoI and the 4.8-kb Xho/XhoI fragment (m.u. 0.77 to m.u. 0.906) (Leung-Tack et al., 1994) is gel purified and cloned into the XhoI site of pGEM7Z to form pKS401. To create a deletion in the BHV-1 gI and gE genes, pKS401 containing the glycoprotein D gene, the gI gene, and most of the gE gene is digested with NruI, and the largest fragment is gel purified and ligated to the 2.5-kb blunt-ended HindIII (T4 Klenow)/EcoRI (Klenow) fragment of pCMV-GUS containing the IEP-regulated β-glucuronidase gene cassette. In the resulting clone (pKS402), the GUS gene is flanked by 1.8 kb (at the amino terminus) and 1.0 kb (at the carboxy terminus) of BHV-1 DNA required for recombination. In addition, a 2-kb region containing the entire gI gene, promoter regulatory sequences, and the coding regions for first 183 amino acids of gE is deleted.

The strategies above are based on the nucleotide sequence data derived from the $U_s$ region of an infectious pustular vulvovaginitis (IPV) (BHV-1 subtype 2) strain (Leung-Tack et al., 1994). The nucleotide sequence of the corresponding $U_s$ region of infectious bovine rhinotracheitis virus (BHV-1 subtype 1) has not been determined or published. Thus, mapping and small scale sequencing of the corresponding regions of the DNA of the Cooper strain of BHV-1 are possibly needed.

In order to generate an in-frame gene fusion (see below) it is necessary to verify the nucleotide sequence of BHV-1 (Cooper strain) coding region of at least the amino terminal end. A 0.46-kb AsuII/NotI fragment is subcloned from pKS401 and the nucleotide sequence is determined by standard methods.

pKS401 is digested with AsuII and treated with Klenow enzyme. The DNA will be redigested with XhoI, and the 1.6-kb fragment is gel purified and cloned into XmnI/SalI-digested pMAL-p2 plasmid (New England Biolabs, Beverly, Ma.). The resultant plasmid (pKS403) is predicted to encode the bacterial maltose-binding protein encoded by the mal E gene in frame with the majority of the gE coding region (533 amino acids). Production of the fusion protein is induced by the addition of IPTG (isopropyl-β-D-thiogalactopyranoside) to medium containing Escherichia coli BL21 carrying pKS403; the fusion protein is affinity purified from bacterial cell lysates using amylose resin according to the recommendations of the manufacturer (New England Biolabs, Beverly, Ma.). New Zealand White rabbits are immunized with the affinity-purified fusion protein as described previously (Chowdhury et al., 1988). Construction of pKS403 is based on the sequence information discussed above. If the sequence is in fact different, the construction strategy is adjusted to yield an in-frame fusion of the mal E and gE genes.

Linearized pKS402 DNA is contransfected with full-length GalTK virus DNA by the $Ca_2PO_4$ precipitation technique in MDBK cells. Recombinant viruses having gI and gE gene sequences deleted are identified as follows: Virus plaques expressing GUS are identified by agar overlay containing 5-bromo-4-chloro-3-indolyl glucuronide (X-Gluc). Briefly, 6-well plates containing a monolayer of MDBK cells are infected with 50–100 PFU's of viruses/well and incubated under overlay medium containing 0.8% agar (low gelling temperature agarose), 300 mg/ml x-Gluc (in DMSO), 40–60 mM Hepes (pH 7.3), 1× MEM (containing 5% FBS and standard concentrations of Penicillin and Streptomycin). Following 2–3 days of incubation, GUS-expressing viruses are collected from blue plaques, sonicated, and small stocks prepared. The recombinant viruses are assayed further for loss of reactivity to gE-specific polyclonal antibody by the white and black plaque method.

Virus from unstained (i.e., white) plaques are plaque purified three times and screened for the gI and gE gene deletions by Western-blot and Southern-blot analyses. A representative gI⁻/gE⁻ derivative is selected as a vaccine strain.

Southern-Blot Hybridization

DNA extracted from purified BHV-1 (Cooper strain) and Gal-TK virions was digested with appropriate restriction enzymes and the fragments were separated on agarose gels and transferred (Southern, 1975) to nylon membranes. Immobilized DNA fragments on membranes were hybridized to DNA probes radioactively labeled with [$\alpha^{32}$P]dCTP by nick-translation (Rigby et al., 1977) using standard procedures (Sambrook et al., 1989).

Animal Experiments

Four newborn calves having the same age to within 1 week were allotted to two groups (A and B) of two calves each. The calves were colostrum-deprived and were found to be negative for BHV-1-neutralizing antibodies at the start of the experiment. Each group was housed separately in isolation rooms with identical conditions. The calves were fed with milk replacer supplemented with antibiotics (Moorman Manufacturing, Quincy, Ill.), and additional antibiotic (Ampicillin; 3 mg/lb body wt) was administered daily for the duration of the study.

At 7 days of age, calves were inoculated with Gal-TK or the Cooper strain of BHV-1 (group B). Inoculation was done by spraying 1 ml of virus suspension ($1\times10^5$ PFUs/ml) in cell culture medium into each nostril of calves in Group A with an inoculation nozzle attached to a syringe. Intensive clinical observation of all calves was performed daily for 14 days following virus exposure. Rectal temperatures were recorded daily. All calves were healthy at the start of the experiment. Special attention was given to behavior, appetite, cough (spontaneous or induced by pressure on the trachea), ocular and nasal discharges, hyperaemia or lesions of the nasal and oral mucosae, conjunctivitis, and abnormal breathing. These parameters were recorded daily for each calf and scored 0 when not present, 1 when mild, 2 when moderate, and 3 when severe. The daily clinical score for each calf was the sum of scores for each parameter. The mean daily clinical score was calculated for each group.

Virus Isolation and Quantitation

Nasal swabs were taken daily for 14 days. A plain cotton-tip swab was inserted into each nasal cavity. The swab was rotated three times against the mucosae. Virus was eluted from the swab in 3 ml of sample medium for 30 min at room temperature, filtered, and assayed daily by standard plaque assay.

Results

Figure 7A:
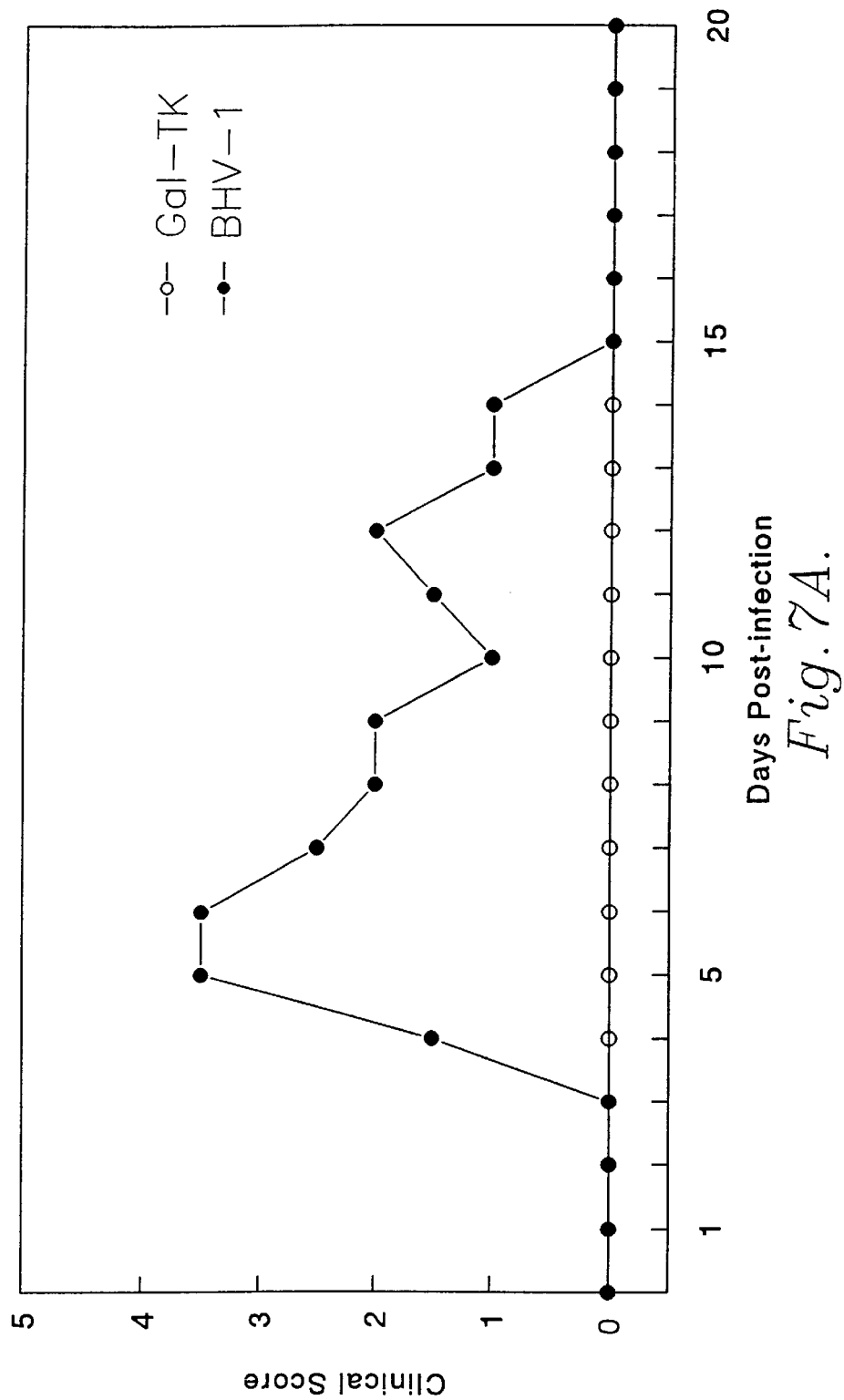
FIGS. 7(A–B) are graphs showing the average daily clinical score (FIG. 7A) and daily rectal temperature (FIG. 7B) of calves after intranasal infection by Gal-TK (○) and BHV-1 (Cooper strain) (●), with each data point representing the average of results obtained from two separate calves.
Figure 7B:
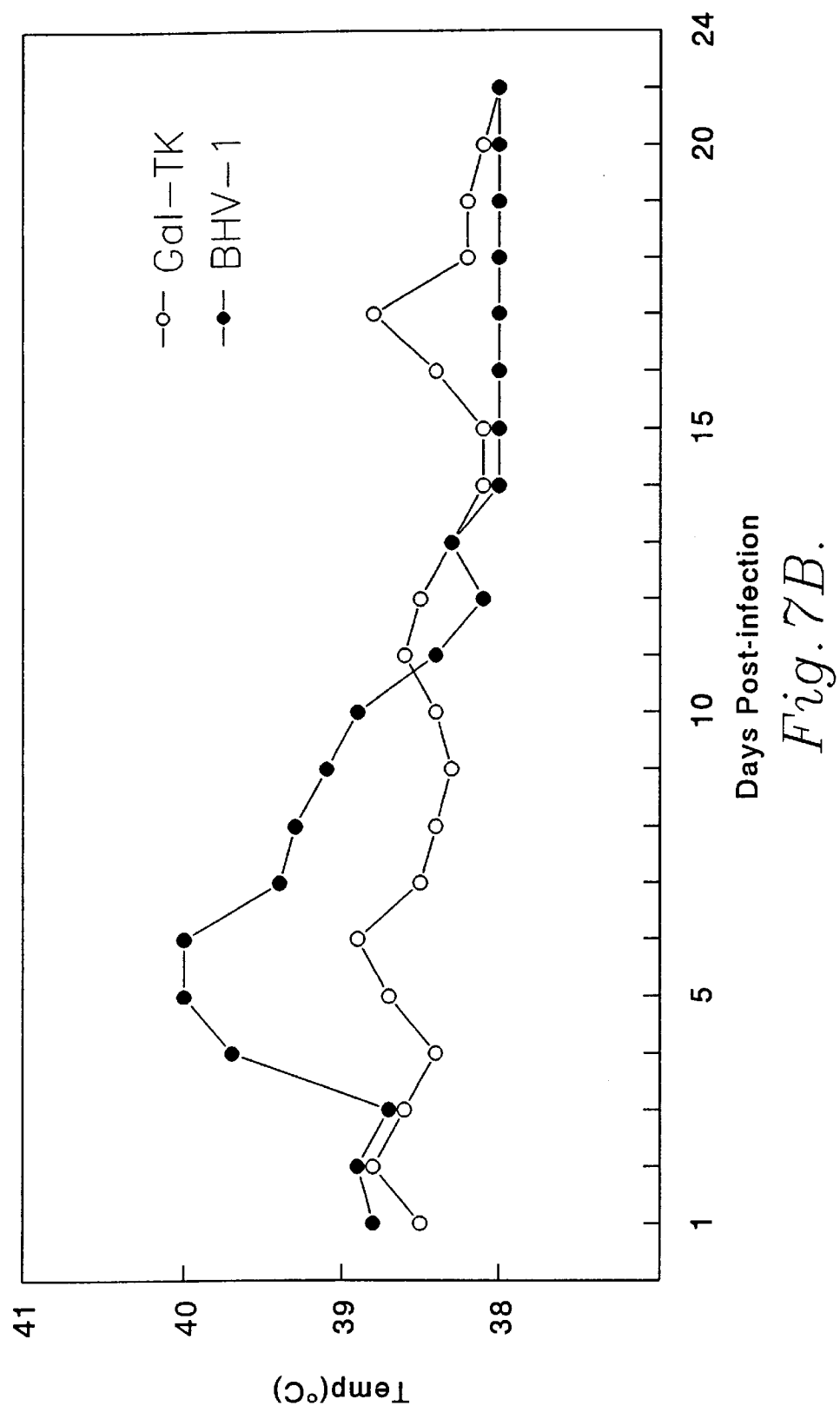

Construction and Characterization of a Recombinant BHV-1 Having a Functional β-gal Gene Inserted in the TK Gene Recombinant BHV-1 viruses generated via homologous recombination were passaged through host cells grown in the presence of AraT and BUdR to select for the growth of TK-inactivated viruses. These viruses then were grown in the presence of Bluo-Gal to identify viruses expressing β-gal (FIG. 3). A recombinant virus (Gal-TK) that yielded blue plaques was selected for further studies. To determine the genetic purity of Gal-TK and to demonstrate that the TK-coding region of this virus was the site of recombination, Southern-blot analyses of Gal-TK DNA restriction fragments using probes specific for BHV-1 TK and β-gal sequences were performed. These results are presented in FIGS. 4(A–B). BHV-1 (Cooper strain) and Gal-TK DNAs, lanes 1 and 2, respectively, were digested with KpnI and HindIII restriction enzymes. DNA fragments were separated by agarose gel electrophoresis and transferred to nylon membranes, and probed with BHV-1 TK-coding sequences (the 2.7-kb SalI fragment of BHV-1 DNA; genomic map units 0.46–0.48) (FIG. 4A) and β-gal-coding sequences (4.5-kb PstI fragment of pCMVβ) (FIG. 4B). Note that the hybridized band in lane 2 of FIG. 4A is 4.5 kb larger than the hybridized band in lane 1 of FIG. 4A as a result of insertion of the β-gal sequence at the TK locus; the former hybridized band corresponds directly to the hybridized band in lane 2 of FIG. 4B. These results conclusively reveal that the recombination event occurred in a site specific manner within the 2.7-kb SalI fragment containing the TK-coding region of BHV-1.

The size of the β-gal gene product and its reactivity with antiserum against β-gal were determined by Western-blot analyses [FIGS. 5 (A–B)]. Polypeptides from lysates of BHV-1 (Cooper strain)-infected (lanes 1), mock-infected (lanes 2), and Gal-TK-infected (lanes 3) MDBK cells were separated electrophoretically on SDS-polyacrylamide gels and transferred to nitrocellulose membranes. The lanes in FIGS. 5(A–B) contain identical amounts of protein. Immunoblotting of membranes was performed with a cocktail of MAbs specific for major BHV-1 glycoproteins B, C, and D (FIG. 5A), and with anti β-gal rabbit polyclonal antibody (FIG. 5B). FIG. 5A shows identical protein profiles for both BHV-1-infected cells (lane 1) and Gal-TK-infected cells (lane 3), indicating that glycoproteins B, C, and D probably are intact in Gal-TK. FIG. 5B shows that a 116-kd protein expressed in the Gal-TK-infected cells (lane 3) reacted specifically with anti-β-gal antibody; this protein comigrated with the 116.5-kd molecular-weight marker protein (β-gal) and was absent in both BHV-1-infected cells (lane 1) and mock-infected cells (lane 2).

The kinetics of β-gal expression in MDBK cells following infection with Gal-TK (5 pfu/cell) were determined. Infected cultures were assayed histochemically for β-gal activity at various times post-infection (3, 6, 12, and 24 h). β-gal activity was present in infected MDBK cells both at early (3 h) and late (24 hrs) stages of infection (data not shown).

Characterization of in vitro Growth of Gal-TK in MDBK Cells

One-step growth experiments were conducted to compare the kinetics of Gal-TK and BHV-1 (Cooper strain) growth in MDBK cells. A series of replicate confluent cultures of MDBK cells were infected separately with 5 PFU/cell of either Gal-TK or BHV-1. After 1 h adsorption at room temperature, residual input viruses were removed. The cultures were washed 5 times with PBS, and 5 ml of medium were added to each flask before further incubation at 37° C. At the time intervals indicated in FIG. 6, replicate cultures were frozen. Virus yields were determined by titration on MDBK cells. The virus growth curves shown in FIG. 6 demonstrate that the time course of progeny virus was similar for Gal-TK and BHV-1. However, the amount of Gal-TK produced was less than the amount of BHV-1 produced throughout the course of the infection. At 28 hours postinfection, the difference was approximately 50-fold.

Pathogenicity of Gal-TK in Calves

BHV-1 (Cooper strain)-infected calves (group B) were severely affected by the infection. Signs of typical BHV-1 infection were observed, including depression, reduced appetite, ocular and nasal discharge, conjunctivitis, necrotic lesions in the nasal mucosa, and mouth-breathing due to obstructed nasal passages. These symptoms resulted in a high daily clinical score over several days (FIG. 7A). However, the calves infected with Gal-TK (group A) did not show any detectable clinical symptoms (FIG. 7A), and their behavior and appetite remained normal.

High rectal temperatures (39.7–40° C.) were recorded for BHV-1 infected calves over several days (FIG. 7B). Rectal temperatures>38.9° C. were never recorded for the Gal-TK-infected calves (FIG. 7B).

Characterization of Gal-TK Replication In Vivo

The amount of virus isolated from nasal swabs demonstrated that Gal-TK grew less efficiently in the nasal epithelial cells compared to BHV-1 (Cooper strain). Shedding of virus in nasal secretions (FIG. 8) was approximately 10 to 400-fold lower for Gal-TK than for BHV-1, and the duration of virus shedding was also shorter for Gal-TK than for BHV-1.

To monitor Gal-TK replication in vivo in calves and to distinguish Gal-TK from BHV-1, cultures infected with viruses isolated from nasal swabs were assayed histochemically for β-gal expression. The results (data not shown) showed that virus isolated from nasal swabs of Gal-TK-infected calves produced typical blue plaques. Similar assays performed during the entire virus-shedding period consistently yielded blue plaque-producing viruses only (data not shown), indicating stable expression of β-gal by Gal-TK even after multiple rounds of in vivo replication in calves.

Discussion

Gal-TK, a recombinant BHV-1 virus has been constructed which contains a functional chimeric reporter/marker gene inserted within the TK gene. The chimeric gene is composed of HCMV-IE promotor and enhancer sequences linked to β-gal and $SV_{40}$ poly-adenylation sequences. The inserted β-gal gene plays no regulatory role in the replication of the virus but serves two purposes. It is useful as a phenotypic marker for Gal-TK, and its insertion resulted in inactivation of the TK gene. The regulation and expression of the chimeric gene are unique to Gal-TK in that (1) the gene is regulated by the strong HCMV-IE promoter and not by any BHV-1-derived regulatory sequence and (2) the β-gal gene is regulated and expressed as an authentic BHV-1 encoded gene at both early and late phases of infection.

In tissue culture experiments, Gal-TK grew less efficiently than the parent BHV-1 virus in MDBK cells. In animal experiments, Gal-TK-infected calves shed less virus and remained healthy, whereas the parental BHV-1-infected calves shed significantly higher amounts of virus and showed typical BHV-1 symptoms and lesions. These results indicate that Gal-TK has been significantly attenuated and is essentially avirulent in immunologically naive calves.

As a consequence of -gal insertion, Gal-TK can produce only a truncated TK consisting of the first 154 aa of the 359 aa encoded by the TK gene. Considering previous reports of TK⁻ mutants, and the selective conditions used to generate Gal-TK in which only TK⁻ viruses can grow (i.e., AraT and BUDR selection), it is probable that the β-gal insertion immediately downstream of the codon encoding aa 154 caused inactivation of the TK gene. Several domains (I–V) in the BHV-1 TK coding region are highly conserved among various herpesviruses (Mittal and Field, 1989). Based on the insertion site of the β-gal gene, early chain termination due to truncation after aa 154 should affect domains IV and V. These domains probably are important for TK function or virulence. Previously, several avirulent BHV-1 TK⁻ mutants obtained in the presence of nucleoside analogues had point mutations in the TK gene resulting in frame shifts or early chain termination (Mittel and Field, 1989). In addition, a deletion of the 343 bp BglII/SacI fragment in the TK gene resulted in avirulent TK⁻ phenotypes (Kit and Kit, 1989). The present study demonstrates that insertion of a functional β-gal gene at the unique BglII site of the BHV-1 TK gene can stably attenuate the virus. The attenuated properties exhibited by Gal-TK paralleled those exhibited by BHV-1 mutants having deletion and point mutations. Further, in situ histochemical detection of β-gal was useful to confirm Gal-TK replication in the nasal mucosa of infected calves, and blot-hybridization experiments with TK⁻ and β-gal-specific probes verified the genetic purity of Gal-TK and distinguished it from the parental BHV-1 strain.

There are several practical applications of Gal-TK. Gal-TK can be used as a vaccine virus since inactivation of its TK gene has resulted in attenuation. Also, synthesis of β-gal by Gal-TK permits easy assessment of Gal-TK replication in the nasal epithelium of vaccinated animals, and detection of R-gal distinguishes infection by Gal-TK from infection by wild-type BHV-1. In addition, the genetic purity of Gal-TK vaccine stock can be easily verified by DNA-hybridization analysis. Furthermore, Gal-TK can be engineered further to serve as a BHV-1-based viral vector to deliver useful gene products of other pathogens to vaccinated animals. Finally, Gal-TK can be further modified by deleting at least part of one or more glycoprotein gene(s) not essential for viral replication (e.g., the glycoprotein E gene, the glycoprotein I gene, and the glycoprotein C gene). A vaccine composed of such a Gal-TK derivative can be used in conjunction with an immunoassay utilizing BHV-1-specific antigen(s) carrying all or part of the glycoprotein(s) missing in the vaccine strain. This immunoassay allows infection by the vaccine strain to be distinguished from infection by wild-type BHV-1 caused by a break in immunity due to a failed vaccine. A BHV-1 vaccine strain lacking a coding region for a particular glycoprotein segment will not elicit antibodies to an antigen carrying this segment, whereas wild-type BHV-1 will; thus, an animal infected with this vaccine strain, but not infected with wild-type BHV-1, will not have antibodies specific for this antigen while an animal infected with wild-type BHV-1 will.

References

The teachings of the following references are herein incorporated by reference:

1. Abdelmagid, O. Y., Minocha, H. C., Collins, J. K., and Chowdhury, S. I. 1995. Fine mapping of bovine herpesvirus-1 (BHV-1) glycoprotein D (gD) neutralizing epitopes by type-specific monoclonal antibodies and sequence comparison with BHV-5 gD. Virology. 206, 242–253.
2. Bello, L. J., Whitbeck, J. C., and Lawrence, W. C. 1992. Sequence and transcript analysis of the bovine herpesvirus 1 thymidine kinase locus. Virology. 189, 407–414.
3. Bello, L. J., Whitbeck, J. C, and Lawrence, W. C. 1987. Map location of the thymidine kinase gene of bovine herpesvirus 1. J. Virol. 61, 4023–4025.
4. Chowdhury, S. I. 1995. Molecular basis of antigenic variation between the glycoproteins C of respiratory bovine herpesvirus 1 (BHV-1) and neurovirulent BHV-5. Virol. 213:558–568.
5. Chowdhury, S. I. and Batterson, W. 1994. Transinhibition of herpes simplex virus replication by an inducible cell-resident gene encoding a dysfunctional VP19C capsid protein. Virus Res. 33, 67–68.
6. Chowdhury, S. I., H. Ludwig, and H.-J. Buhk. 1988. Molecular biological charaterization of equine herpesvirus type 1 (EHV-1) isolated from ruminant hosts. Virus Res. 11: 127–139.
7. Chowdhury, S. I., Kubin, G. and Ludwig, H. 1986. Equine herpesvirus type 1 (EHV-1) induced abortions and paralysis in a Lipizzaner stud: a contribution to the classification of equine herpesviruses. Arch. Virol. 90, 273–288.
8. Field, H. J. and Wildy, P. 1978. The pathogenesis of thymidine kinase-deficient mutants of herpes simplex virus in mice. J. Hygiene. 81, 267–277.
9. Fitzpatrick, D. R., Babiuk, L. A., and Zamb, T. 1989. Nucleotide sequence of bovine herpesvirus type 1 glycoprotein III, a structural model for gIII as a new member of the immunoglobulin superfamily, and the implication for the homologous glycoproteins of other herpesviruses. Virol. 173, 46–57.
10. Holland, T. C., Sandri-goldin, R. M., Holland, L. E., Marlin, S. D., Levine, M., and Glorioso, J. C. 1983. Physical mapping of the mutation in an antigenic variant of herpes simplex virus type 1 by use of an immunoreactive plaque assay. J. Virol. 16, 649–652.
11. Kit, M. and Kit, S. 1987. Thymidine kinase deletion mutants of bovine herpesvirus-1. U.S. Pat. No. 4,703,011.
12. Kit, M. and Kit, S. 1989. Thymidine kinase deletion mutants of bovine herpesvirus-1, vaccines against infectious bovine rhinotracheitis containing same and methods for the production and use of same. U.S. Pat. No. 4,824,667.
13. Kit, S. and Qavi, H. 1983. Thymidine kinase (TK) induction after infection of TK-deficient rabbit cell mutants with bovine herpesvirus type 1 (BHV-1); isolation of TK⁻ BHV-1 mutants. Virology. 130, 381–389.
14. Kit, S., Kit, M., and Pirtle, E. G. 1985a. Attenuated properties of thymidine kinase-negative deletion mutant of pseudorabies virus. Am. J. Vet. Res. 6, 1359–1367.
15. Kit, S., Qavi, H., Gaines, J. D., Billingsley, P., and McConell, S. 1985b. Thymidine kinase-negative bovine herpesvirus type 1 mutant is stable and highly attenuated in calves. Arch. Virol. 86, 63–83.
16. Kousoulous, K. G., Pellet, P. E., Pereira, L., and Roizman, B. 1984. Mutations affecting conformation or sequence of neutralizing epitopes identified by reactivity of viable plaques segregate from Syn and ts domains of HSV-1 (F) gB gene. Virol. 135, 379–394.
17. Laemli, U. K. 1970. Cleavage of structural proteins during the assembly of the head of bacteriophage T4. Nature (London) 227, 680–685.
18. Leung-Tack, P., Audonnet, J., and Riviere, M. 199. The complete DNA sequence and the genetic organization of the short unique region ($U_s$) of the bovine herpesvirus type 1 (ST strain). Virology 1994, 409–421.
19. Ludwig, H. 1983. Bovine herpesviruses. In The Herpesviruses. Vol II, Roizman, B. (ed). p 135–214. Plenum Press. New York.
20. Mayfield, J. E., Good, P. J., VanOort, H. J., Campbell, A. R., and Reed, D. E. 1983. Cloning and cleavage site mapping of DNA from bovine herpesvirus 1 (Cooper strain). J. Virol. 47, 259–264.
21. Misra, V., Blumenthal, R. M., and Babiuk, L. A. 1981. Proteins specified by bovine herpesvirus 1 (infectious bovine rhinotracheitis). J. Virol. 40, 367–378.
22. Mittal, S. K. and Field, H. J. 1989. Analysis of the bovine herpesvirus type 1 thymidine kinase (TK) gene from wild-type virus and TK-deficient mutants. J. Gen. Virol. 70, 901–918.
23. Rigby, P. W. J., Diekmann, M., Rhodes, C., and Berg, P.1977. Labeling deoxy-ribonucleic acid to high specific activity in vitro by nick translation with DNA polymerase I. J. Mol. Biol. 113, 237.
24. Sambrook, J., Fritsch, E., and Maniatis, T. 1989. Molecular cloning: A laboratory manual. Cold Spring Harbor Laboratories, Cold Spring Harbor, N.Y.
25. Smith, G. A., Young, P. L., and Mattick, J. S. 1990. The location and nucleotide sequence of the thymidine kinase gene of bovine herpesvirus type 1.2. J. Gen. Virol. 71, 2417–2424.
26. Southern, E. M. 1975. Detection of specific sequences among DNA fragments separated by gel electrophoresis. J. Mol. Biol. 98, 503–517.
27. Weinmaster, G. A., Misra, V., McGuire, R., Babiuk, L. A., and DeClercq, E. 1982. Bovid herpesvirus type-1 (infectious bovine rhinotracheitis virus)-induced thymidine kinase. Virology. 118, 191–201.
28. Whitbeck, J. C., Lawrence, W. C., and Bello, L. 1994. Characterization of the bovine herpesvirus 1 homology of the herpes simplex virus 1 UL24 open reading frame. Virology. 200, 263–270.
29. Wyler, R., Engels, M., and Schwyzer, M. 1989. Infectious bovine rhinotracheitis/vulvovaginitis (BHV-1). In Whittmann, G. (ed). Herpesvirus Diseases of Cattle, Horses, and Pigs. Developments in Veterinary Virology. p 1–172. Kluwer Academic Publishers, Boston.

What is claimed is:

1. An infectious recombinant bovine herpesvirus comprising a foreign gene inserted into and inactivating a bovine herpesvirus gene in the virus genome, said foreign gene comprising a human cytomegalovirus immediate early promoter and a β-galactosidase coding region, wherein said foreign gene is expressed at both early and late phases of infection as an authentic bovine herpesvirus gene, said β-galactosidase coding region being derived from an organism different from humans and bovine herpesvirus, said human cytomegalovirus immediate early promoter being from a different organism than said bovine herpesvirus and said β-galactosidase coding region, said recombinant bovine herpesvirus being capable of transfecting a host cell.

2. The bovine herpesvirus of claim 1, wherein said bovine herpesvirus is a bovine herpesvirus type 1.

3. The bovine herpesvirus of claim 1, wherein said bovine herpesvirus gene is a thymitive kinase gene.

4. The bovine herpesvirus of claim 1, wherein said β-galactosidase gene is an *Escherichia coli* β-galactosidase gene.

5. The bovine herpesvirus of claim 1, wherein said inactivated bovine herpesvirus gene is the bovine herpesvirus gene of pGal-TK.

6. The bovine herpesvirus of claim 1, wherein said bovine herpesvirus is Gal-TK.

7. The bovine herpesvirus of claim 1, wherein said bovine herpesvirus is attenuated.

8. The bovine herpesvirus of claim 7, wherein said bovine herpesvirus is essentially avirulent.

9. The bovine herpesvirus of claim 6, wherein the glycoprotein C gene is at least partially deleted from said bovine herpesvirus.

10. A vaccine comprising an infectious recombinant bovine herpesvirus in a pharmaceutically acceptable carrier, said infectious recombinant bovine herpesvirus comprising a foreign gene inserted into and inactivating a gene in the virus genome, said foreign gene comprising a human cytomegalovirus immediate early promoter and a β-galactosidase coding region derived from a first organism different than humans or bovine herpesvirus, said herpesvirus being capable of transfecting a host cell wherein said foreign gene is expressed in said host cell at both early and late phases of infection.

11. The vaccine of claim 10, wherein said pharmaceutically acceptable carrier is cell culture medium.

12. The vaccine of claim 10, wherein the glycoprotein C gene is at least partially deleted from said bovine herpesvirus.

13. The vaccine of claim 10, wherein said bovine herpesvirus gene is a thymidine kinase gene.

14. The vaccine of claim 10, said coding region from *E. coli* β-galactosidase gene.

15. A method of immunizing an animal against diseases caused by bovine herpesvirus, comprising the step of administering to said animal a vaccine of claim 10.

16. The method of claim 15, wherein said administering step comprises spraying said vaccine into the nostrils of said animal.

17. The method of claim 15, wherein a glycoprotein gene not essential for viral replication is at least partially deleted from said infectious recombinant bovine herpesvirus.

18. The method of claim 15, wherein said glycoprotein gene is selected from the group consisting of the glycoprotein E gene, the glycoprotein I gene, and the glycoprotein C gene.

* * * * *